United States Patent
Kim et al.

(10) Patent No.: US 12,251,452 B2
(45) Date of Patent: *Mar. 18, 2025

(54) METHOD FOR ENHANCING OPTICAL PROPERTIES IN CERAMICS HAVING APPLICATIONS IN DENTAL RESTORATIONS

(71) Applicant: James R. Glidewell Dental Ceramics, Inc., Newport Beach, CA (US)

(72) Inventors: Jae Won Kim, Irvine, CA (US); Akash, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,541

(22) Filed: Nov. 17, 2022

(65) Prior Publication Data

US 2023/0078408 A1    Mar. 16, 2023

Related U.S. Application Data

(63) Continuation of application No. 15/923,345, filed on Mar. 16, 2018, now Pat. No. 11,504,304.

(Continued)

(51) Int. Cl.
| | |
|---|---|
| *A61K 6/78* | (2020.01) |
| *A61K 6/818* | (2020.01) |
| *A61K 6/822* | (2020.01) |
| *B05D 1/02* | (2006.01) |
| *B05D 1/28* | (2006.01) |
| *B05D 3/02* | (2006.01) |
| *C04B 41/00* | (2006.01) |
| *C04B 41/50* | (2006.01) |
| *C04B 41/51* | (2006.01) |
| *C04B 41/52* | (2006.01) |
| *C04B 41/88* | (2006.01) |

(Continued)

(52) U.S. Cl.
CPC ............... *A61K 6/78* (2020.01); *A61K 6/818* (2020.01); *A61K 6/822* (2020.01); *B05D 1/02* (2013.01); *B05D 1/28* (2013.01); *B05D 3/0272* (2013.01); *C04B 41/009* (2013.01); *C04B 41/5012* (2013.01); *C04B 41/515* (2013.01); *C04B 41/52* (2013.01); *C04B 41/88* (2013.01); *C04B 41/89* (2013.01); *C04B 2111/00836* (2013.01); *C04B 2111/80* (2013.01)

(58) Field of Classification Search
CPC ......................................................... A61K 6/78
See application file for complete search history.

(56) References Cited

U.S. PATENT DOCUMENTS

| | | | |
|---|---|---|---|
| 3,875,971 | A | 4/1975 | Hamling |
| 4,557,691 | A | 12/1985 | Martin et al. |

(Continued)

FOREIGN PATENT DOCUMENTS

WO    2014022643 A1    2/2014

*Primary Examiner* — Dah-Wei D. Yuan
*Assistant Examiner* — Andrew J Bowman
(74) *Attorney, Agent, or Firm* — Klarquist Sparkman, LLP (57) ABSTRACT

A method for enhancing optical properties of sintered, zirconia ceramic bodies and zirconia ceramic dental restorations is provided. The porous or pre-sintered stage of a ceramic body is treated with an yttrium-containing composition and sintered, resulting in sintered ceramic bodies having enhanced optical properties. The enhanced optical properties may be substantially permanent, remaining for the useful life of the sintered ceramic body.

18 Claims, 8 Drawing Sheets

Related U.S. Application Data

(60) Provisional application No. 62/472,195, filed on Mar. 16, 2017, provisional application No. 62/472,100, filed on Mar. 16, 2017.

(51) Int. Cl.
*C04B 41/89* (2006.01)
*C04B 111/00* (2006.01)
*C04B 111/80* (2006.01)

(56) References Cited

U.S. PATENT DOCUMENTS

| | | |
|---|---|---|
| 6,709,694 B1 | 3/2004 | Suttor et al. |
| 6,908,872 B2 | 6/2005 | Tanaka et al. |
| 8,298,329 B2 | 10/2012 | Knapp et al. |
| 8,696,954 B2 | 4/2014 | Tanaka |
| 8,697,176 B2 | 4/2014 | Wang et al. |
| 8,835,004 B2 | 9/2014 | Dittmann et al. |
| 8,936,848 B2 | 1/2015 | Jung et al. |
| 9,095,403 B2 | 8/2015 | Carden et al. |
| 9,212,065 B2 | 12/2015 | Yamada et al. |
| 9,365,459 B2 | 6/2016 | Carden et al. |
| 9,434,651 B2 | 9/2016 | Carden |
| D769,449 S | 10/2016 | Leeson et al. |
| 9,512,317 B2 | 12/2016 | Carden et al. |
| 9,554,881 B2 | 1/2017 | Wang et al. |
| 9,597,265 B2 | 3/2017 | Carden et al. |
| 9,872,746 B2 | 1/2018 | Hauptmann et al. |
| 10,034,728 B2 | 7/2018 | Jung et al. |
| 11,504,304 B2 | 11/2022 | Kim et al. |
| 2010/0221683 A1 | 9/2010 | Franke et al. |
| 2014/0101869 A1 | 4/2014 | Carden et al. |
| 2015/0079408 A1 | 3/2015 | Piascik et al. |
| 2015/0157430 A1 | 6/2015 | Hauptmann et al. |
| 2016/0002112 A1 | 1/2016 | Stephan |

METHOD FOR ENHANCING OPTICAL PROPERTIES IN CERAMICS HAVING APPLICATIONS IN DENTAL RESTORATIONS

RELATED APPLICATIONS

This application is a continuation of and claims the benefit of, and priority to, U.S. patent application Ser. No. 15/923,345, filed Mar. 16, 2018, which claims the benefit of, and priority to, U.S. Provisional Patent Application No. 62/472,195, filed Mar. 16, 2017, and U.S. Provisional Patent Application No. 62/472,100, filed Mar. 16, 2017, the entireties of each of which applications are incorporated herein by reference.

BACKGROUND

Ceramic bodies that are colorized by known processes before or after sintering show a decrease in translucency upon application of the colorant. Post-sintering treatments to enhance a translucent effect are often temporary, failing to last the useful life of the restoration. Other translucency enhancing treatments mimic enhanced translucency without actually increasing percent transmittance.

SUMMARY

A method for making highly translucent sintered ceramic bodies is provided. The sintered ceramic bodies are suitable for use in dental restorations. Enhanced properties may be substantially permanent for the useful life of the restoration. A method is provided for treating a pre-sintered ceramic body with an yttrium-containing composition; after sintering, the ceramic body has greater yttria concentration where the yttrium-containing composition was applied, and a higher percent transmittance than an untreated ceramic body of the same ceramic material. Sintered restorations made by the methods described herein have a color space (CIE L*a*b*) values within a desired range, and have suitable strength in the final sintered ceramic dental restoration for use in anterior and/or posterior dental applications. Thus, methods and compositions are described for forming sintered ceramic dental restorations in selected shades that have enhanced translucency and suitable strength.

DETAILED DESCRIPTION

Figure 1:
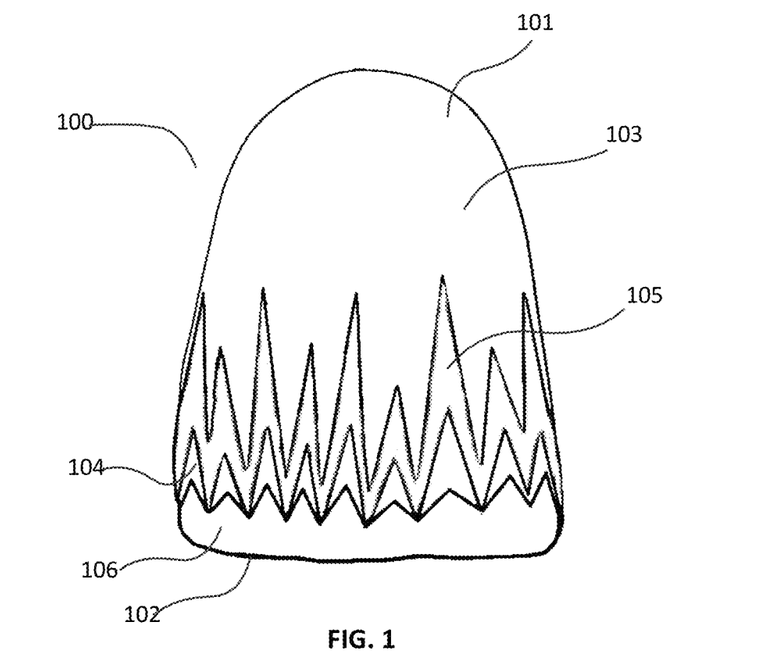
FIG. 1. Front view of an illustration of a dental restoration.

With reference to FIG. 1, a method is provided for treating a pre-sintered or bisque stage zirconia ceramic body, such as a dental restoration (100), by applying an yttrium-containing composition to the bisque ceramic body, and, then, sintering to approximately full density. The yttrium-containing composition comprises an yttrium-containing material and, optionally, a colorant. In one embodiment, the yttrium-containing composition comprises an yttrium chloride aqueous solution or sol, and one or more colorants. The treated, sintered ceramic body has a natural tooth shade and greater translucency than an untreated, sintered ceramic body having a similar shade.

The yttrium-containing composition comprises an amount of an yttrium-containing material that is sufficient to impart high transmittance in a sintered ceramic body, when tested according to the methods described herein. The yttrium-containing composition may comprise approximately 5% by weight (wt %) to approximately 70% by weight of the yttrium-containing material, such as an yttrium salt, based on the total weight of the yttrium-containing composition. In other embodiments, the amount of yttrium-containing material may be between 10 wt. % and 70 wt. %, based on the total weight of the yttrium-containing composition, or between approximately 20 wt. % and 70 wt. %, or between approximately 30 wt. % and approximately 70 wt. %, or between approximately 40 wt. % and approximately 70 wt. %, or between approximately 50 wt. % and approximately 70 wt. %, or between approximately 20 wt. % and approximately 60 wt. %, or between approximately 20 wt. % and approximately 65 wt. %, or between approximately 20 wt. % and approximately 40 wt. %, or between approximately 40 wt. % and approximately 60 wt. %, or between approximately 50 wt. % and approximately 60 wt. %, based on the total weight of the yttrium-containing composition. Yttrium-containing materials include, but are not limited to, yttrium salts, such as yttrium chloride, including yttrium chloride hexahydrate (e.g., yttrium (III) chloride hexahydrate), yttrium nitrate (e.g., yttrium (III) nitrate hexahydrate), and yttrium carbonate (e.g., yttrium (III) carbonate hydrate).

The one or more colorants of the yttrium-containing composition comprise at least one coloring agent that may be selected for example, to achieve a specific lightness, hue or chroma value of the ceramic material in the final sintered body. The colorant may be selected to impart a shade suitable for use in dental restorations, such as a shade based on an industry-recognized shade guide, such as the VITA Classical Shade Guide. Colorants may include coloring agents and coloring liquids, described in commonly owned US Patent Publication Nos. 2013/0231239, 2014/0109797, and U.S. Pat. No. 9,095,403, each of which is incorporated by reference herein in their entirety.

Colorants may comprise at least one coloring agent comprising a metal-containing component, including metallic compounds and metallic complexes. Metal-containing components may comprise metallic salts that contain transition metals from groups 3-14 on the periodic table, rare earth metals, and mixtures thereof. For example, coloring agents may comprise metal-containing components in the form of oxides or salts of metals including but not limited to, iron, terbium, erbium, chromium, cobalt and manganese. Metal-containing components in the form of oxides or salts may contain anions, including but not limited to $Cl^-$, $SO_4^{2-}$, $SO_3^{2-}$, $Br^-$, $F^-$, $NO_2^-$, and $NO_3^-$.

In one embodiment, the at least one metallic salt comprises one or more metals selected from chromium, terbium, and manganese. Terbium, chromium and manganese may be present as a form of terbium chloride, chromium chloride, and manganese sulfate, respectively.

The at least one metallic salt may be added in an amount in the range of approximately 0.05 wt. % to approximately 2 wt. % metallic salt based on the total weight of the yttrium-containing composition, or approximately 0.07 wt. % to approximately 1 wt. % metallic salt based on the total weight of the yttrium-containing composition. Alternatively, the amount of metallic salt is in a range of approximately 0.1 wt. % to 0.5 wt. % metallic salt based on the total weight of the yttrium-containing composition.

Coloring liquids to be incorporated into yttrium-containing compositions may be prepared as aqueous coloring solutions having no solid colorant particles that are detectable at ambient temperature to the unaided eye after mixing a coloring agent with a solvent. Multiple coloring liquids may be prepared and incorporated with the yttria-containing composition to provide a range of natural tooth shades, providing color to ceramic materials that are otherwise deemed to have an unacceptable shade if used in dental applications in the uncolored stage. When coloring liquids are applied to a porous unshaded or porous shaded zirconia ceramic body, after sintering the colorized ceramic bodies may match, for example, a Vita Classical shade such as BL1, BL2, BL3, and BL4 (bleach shades) and A1-D4 shades (e.g. A1, A2, A3, A3.5, A4, B1, B2, B3, B4, C1 C2, C3, C4, D2, D3, and D4) (e.g., from Vita Classical shade guide).

Optionally, acids, such as citric acid may be added to increase the solubility of the colorant, or the solubility of the yttrium-containing component, or both the colorant and the yttrium-containing component. For example, an aqueous yttrium-containing composition may comprise approximately 0.05M to approximately 5M citric acid, or from approximately 0.5M to approximately 5M citric acid, or from approximately 0.5M to approximately 2M citric acid. Organic solvent or non-organic solvent may also be added to the liquid coloring solution or the yttrium-containing composition, for example, to increase solubility of the yttrium-containing material and/or coloring agents to reduce or eliminate visible particles.

In one embodiment, the yttrium-containing composition comprises an aqueous solution or sol of yttrium salt wherein the yttrium salt is in an amount between approximately 45 wt. % and approximately 70 wt. %, based on the total weight of yttrium-containing composition, 0.05M to 5M citric acid, and a coloring agent comprising at least one metal oxide or metal salt. In another embodiment, the yttrium-containing composition comprises an aqueous solution of yttrium salt in an amount between approximately 60 wt. % and approximately 70 wt. %, based on the total weight of yttrium-containing composition, 0.22 to 2M citric acid, and a coloring agent comprising at least one metal oxide or metal salt.

Yttrium-containing compositions are applied to green (unsintered) ceramic bodies, or pre-sintered ceramic bodies that that retain at least partial porosity for penetration of the yttrium-containing composition into the thickness of the material form.

Zirconia ceramic bodies comprise ceramic materials including, but not limited to zirconia, partially stabilized or stabilized zirconia, including yttria-stabilized tetragonal zirconia, and mixtures thereof. Examples of partially stabilized or stabilized zirconia suitable for use herein include commercially available ceramic materials from Tosoh USA, such as zirconia that has been stabilized with yttria, (e.g., YSZ zirconia from Tosoh) including approximately 0.1 mol % to approximately 8 mol % yttria, or approximately 2 mol % to approximately 7 mol % yttria, or from approximately 2 mol % to approximately 6 mol % yttria, or fro a approximately 2 mol % to approximately 5 mol % yttria, or from approximately 3 mol % to approximately 5 mol % yttria, or from approximately 3 mol % yttria to approximately 4 mol % yttria, or from approximately 4 mol % yttria to approximately 5 mol % yttria, or from approximately 3.5 mol % yttria to approximately 5 mol % yttria. In one embodiment, ceramic bodies are made from zirconia that has been stabilized with approximately 1 mol % to approximately 3 mol % yttria.

Zirconia ceramic bodies may be made from ceramic materials that comprise approximately 85 wt. % to approximately 100 wt. % zirconia or stabilized zirconia, based on the total weight of the zirconia ceramic material, or approximately 85 wt. % or greater, or approximately 90 wt. % or greater, or approximately 95 wt. % or greater, or more than approximately 97 wt. % or greater zirconia or stabilized zirconia, based on the total weight of the zirconia ceramic material. Other materials, such as, alumina may also be included in the zirconia ceramic material.

Zirconia ceramic bodies may be formed from zirconia powder having a substantially uniform particle size distribution, such as powder with an average size in a range from approximately 0.005 micron (μm) to approximately 1 μm. Examples of ceramic material suitable for use herein also include zirconia described in commonly owned U.S. Pat. No. 8,298,329, which is hereby incorporated by reference in its entirety.

Ceramic powder may be made into a ceramic body shaped as a block, disk, near net shape, or a form that approximates the size and/or shape of a single or multi-unit dental restoration, such as a crown, on-lay, bridge including a multi-unit bridge comprising restorations having more than one tooth structure, partial or full solid-body denture. Porous ceramic bodies may be made by processes including but not limited to uniaxial or biaxial pressing or slip casting, and automated processes, including additive (e.g., 3-D printing) and subtractive (e.g., milling) automated processes. Processes for making ceramic bodies suitable for use herein include those described in commonly owned U.S. Pat. Nos. 9,365,459, 9,434,651, and 9,512,317, all of which are hereby incorporated in their entirety, herein. Commercially available pre-sintered or bisque state ceramic bodies include those that have been heated to increase the density of a green body to below the full theoretical density of a fully sintered ceramic body in accordance with suggestions provided by the manufacturer. Pre-sintered ceramic bodies include those having a density of approximately 30% to 90%, or approximately 50% to 90%, of full theoretical density.

The pre-sintered ceramic bodies may be shaped in the form of a dental restoration, such as a single unit crown, based on the individual requirements of a patient, by milling or automated processes, including CAD and/or CAM processes, prior to application of the yttrium-containing composition. Alternatively, the ceramic bodies may be sintered to approximately full theoretical density after application of the yttrium-containing composition, prior to milling into a dental restoration by making a ceramic preform having a size and shape that accommodates most custom restorations. Examples of suitable shaped forms which may be sintered to full theoretical density prior to shaping to a final dental restoration form may be found in commonly owned U.S. Patent Publication No. 2013/0316305, and U.S. Pat. No. D769,449, both of which are hereby incorporated herein in their entirety.

Pre-sintered, porous ceramic bodies may be made from unshaded (uncolored) or white ceramic powder. Alternatively, pre-colored ceramic powders that are shaded to match a target or desired shade in a final sintered body may be pressed or shaped into a porous body for used herein, and include commercially available ceramic blocks, such as BruxZir® Shaded 16 series porous ceramic bodies (Glidewell Laboratories, Irvine, CA) that match the VITA Classic shades in a final restoration. Other pre-shaded ceramic powders are used for achieving a range of final dental shades in the sintered body, and the precise target shade is attained by additional coloring or staining before or after sintering. Pre-shaded ceramic materials may advantageously provide uniform shade distribution throughout the sintered ceramic body Colorants added to the yttrium-containing composition may be selected to match existing dentition, or to impart a natural or desired appearance, or to achieve a specific target shade (e.g., Vita Classical Shade Guide shade of, for example A1, or A2, or bleach shades.) To achieve a target shade in a final restoration, the concentration of coloring agent added to an yttrium-containing composition may be greater for ceramic bodies made from unshaded ceramic powder than ceramic bodies formed from a shaded ceramic powder, for a given target shade. Where the application of yttrium-containing composition has a lightening effect on a shaded ceramic body, yttrium-containing compositions having lower Tight percent yttrium may require the addition of a lower weight percent coloring agent to achieve a target shade.

Figure 2:
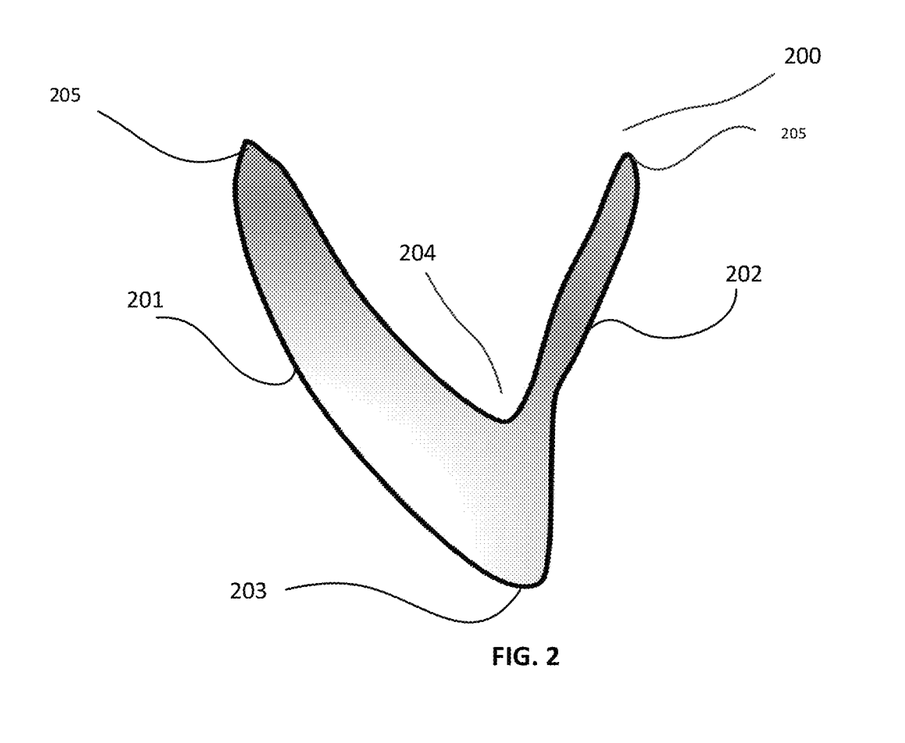
FIG. 2. Cross-sectional illustration of a dental restoration.

Application techniques for applying the yttrium-containing composition to penetrate the porous, pre-sintered ceramic bodies include, but are not limited to, painting, dipping, spraying, or infiltrating the ceramic body with the yttrium-containing composition by other known application methods. In one embodiment, illustrated in FIG. 2, the cross-sectional view of a shaped ceramic body in the form of a dental restoration, one or more applications of the yttrium-containing composition may be applied to one or more of the external buccal/labial (201), lingual (202), or distal or mesial, surfaces of a dental restoration form (200). The composition may be applied from the edge of the crown margin (101, 205) area completely coating a restoration surface to the incisal or occlusal edge (together, may be referred to herein as biting edge for convenience) (102, 203). Alternatively, the composition may be applied only to an area of the buccal or labial surface (which together, may be referred to herein as facial surface for convenience) (103) that is visible when the final sintered body is fitted in the mouth of a patient. In an embodiment, approximately one half to approximately one third of a buccal or labial surface (104, 105) proximate the incisal or occlusal edge (biting edge) (102, 203) is treated, or alternately, only the tooth area that is visible upon sintering, is treated. In one embodiment, the yttrium-containing composition may be applied to an internal surface or cavity (204) of a dental restoration, specifically, an internal surface or cavity surface that abuts a tooth preparation for attachment in the mouth of a patient.

In another embodiment, pre-sintered ceramic bodies shaped as pre-forms or near net shapes may also be treated with the yttrium-containing compositions. In one embodiment, the pre-form or near net shape may be dipped in a yttrium-containing composition to achieve partial or complete penetration through the thickness of a body. In another embodiment, the yttrium-containing composition may be applied to one or more sides or surfaces of a pre-form or near net shape that corresponds with an area that an occlusal or buccal surface of a restoration is ultimately milled from the ceramic body. In this embodiment, pre-sintered ceramic bodies may be sintered after treatment with the yttrium-containing composition, prior to milling or grinding to form a patient-specific dental restoration.

In another embodiment, a second or subsequent application of the same yttrium-containing composition may be applied to penetrate the porous ceramic body before the first application that has penetrated the porous ceramic body completely dries. Without wishing to be bound by theory, it is believed that in one embodiment, where a second or subsequent application applied to penetrate a portion of the porous ceramic body that comprises the first application of the yttrium-containing component (i.e., before the solvent of the first application dries), an edge of the region of the second application mixes or blends with a portion of the first application, and provides smooth transition between the first and second application. The smooth transition between the first and second application may form a color and/or translucency gradient in a final sintered body. In an alternate embodiment, a first application is applied to a porous ceramic body and is dried (i.e., the solvent is removed from the porous ceramic structure) before a second application is applied to only a portion of the first application. Where no mixing or blending of liquid compositions occurs at the edge of the second application, a step-wise or layered shift in translucency or colorant may result between the first and second application regions in the final sintered body.

In one embodiment, a porous zirconia ceramic body in the form of a dental restoration, such as a crown or a tooth-shaped form, may be completely dipped to apply a second or subsequent coating of the yttrium-containing composition to the entire external and optionally internal surface of the dental form. In another embodiment, second or subsequent application(s) are applied to a surface that is visible when the final sintered body is fitted in the mouth of a patient. Multiple application(s) of the yttrium-containing composition may be brushed or otherwise applied at the biting edge (e.g., incisal edge) (102), adjacent the biting surface, of the restoration for a distance of approximately 0.5 mm to approximately 3 mm, or for a distance of approximately 0.5 mm to approximately 4 mm, or for a distance of approximately 0.5 mm to approximately 5 mm, or for a distance of approximately 1 mm to approximately 5 mm, from the biting edge (102). For example, the yttrium-containing composition may be applied for a distance of approximately 1 mm, or approximately 1.5 mm, or approximately 2 mm, or approximately 2.5 mm, or approximately 3 mm, from the biting edge. The yttrium-containing composition may be applied, for example, by brushing in even or uneven patterns, such as a zigzag pattern or a jagged pattern in FIG. 1 (at 104, 105, 106). Optionally, one or more of the regions is applied by a technique that provides a jagged or zigzag edge between adjacent regions as seen in FIG. 1. Multiple applications of the yttrium-containing composition may result in a sintered body having a first region (106) proximate the biting (e.g., incisal) edge (102) having a first concentration of yttria that is greater than adjacent regions having a greater distance from the biting edge, such as a second region (104), a third (105) region, and subsequent regions (103), each of which may have increasingly lower concentrations of yttria as the distance from the biting (e.g., incisal) edge increases. In one embodiment, a method is provided for enhancing the translucency of a porous zirconia ceramic body made of an yttria-stabilized zirconia material comprising 2 mol % yttria to 7 mol % yttria, wherein the method steps include applying an aqueous yttrium-containing composition comprising 20% wt to 70% wt yttrium-containing material and a colorant that comprises at least one metal-containing component as a coloring agent. The method comprises applying a first application of the yttrium-containing composition penetrate a portion of the porous zirconia ceramic body, and applying a second application of the yttrium-containing composition to penetrate the portion of the porous zirconia ceramic body that comprises the aqueous yttrium-containing composition of the first application. In one embodiment, the yttria-stabilized zirconia material is pre-shaded and the yttrium-containing composition comprises between 40 wt. % and 70 wt. % of the yttrium-containing material. In another embodiment, the yttria-stabilized zirconia material is pre-shaded and comprises between 3 mol % yttria and 5 mol % yttria, and the yttrium-containing composition comprises between 20 wt % and 40 wt. % of an yttrium-chloride. In a further embodiment, the yttria-stabilized zirconia material is an unshaded, white zirconia ceramic material and the yttrium-containing composition comprises between 20 wt. % and 65 wt. % of the yttrium-containing material based on the total weight of yttrium-containing composition. In one embodiment, the porous zirconia ceramic body is in the shape of a dental restoration having an incisal edge and a facial surface, and the method comprises applying a first application of the yttrium-containing composition to the facial surface of the dental restoration from an incisal edge to a distance of one-third to one-half the length of the facial surface proximate the incisal edge, and the second application penetrates a portion of the porous ceramic body that comprises the aqueous yttrium-containing composition from the first application. In a further embodiment, the first application is applied to the facial surface from the biting edge for a first distance of 1 mm to 5 mm from the biting edge, and the second application is applied to the facial surface from the biting edge for a second distance of 0.5 mm to 3 mm that is less than the first distance.

The yttrium-containing composition wets a porous ceramic body, for example, by absorbing, infiltrating, diffusing, or otherwise penetrating into the porous ceramic. Multiple applications may be applied to wet through the ceramic body to a specific depth, or through the entire thickness, or until no additional amount of the yttrium-containing composition absorbs or diffuses into the structure of the bisque stage ceramic.

An application method for applying an yttria-containing composition to enhance optical properties of a sintered zirconia ceramic body, is provided. In one embodiment, the method comprises applying a first application of an aqueous yttria-containing composition to an edge of a porous ceramic dental restoration form comprising an yttria-stabilized zirconia ceramic material for a first application distance of 1 mm to 5 mm from the edge, and penetrating a portion of the porous body, wherein the yttrium-containing composition comprises 30% wt to 70% wt yttrium-containing material and a colorant comprising at least one metal-containing component as a coloring agent. The method further comprises applying a second application of the yttria-containing composition to the edge for a second application distance of 0.5 mm to 3 mm from the edge, infiltrating a portion of the porous yttria-stabilized zirconia ceramic body containing the aqueous yttrium-containing composition from the first application, wherein the second distance is less than the first distance. The application method provides for enhanced translucency in the sintered dental restoration, for example, in the region proximate the incisal edge. The application method results in a transmittance of at least 46% or greater at 700 nm, when tested according to the method described herein as applied to a porous ceramic body made from the yttria-stabilized zirconia ceramic material having a 1 mm target thickness and sintered to at least 98% theoretical density. In one embodiment, the yttria-stabilized zirconia ceramic material is a pre-shaded zirconia ceramic material, the yttrium-containing material is 40% wt to 70% wt, and the application method provides at least 50% or greater transmittance at 700 nm after sintering, when tested according to the method described herein as applied to a porous ceramic body made of the pre-shaded zirconia ceramic material shaped to a target thickness of 1 mm. In a further embodiment of the method, the yttria-stabilized zirconia ceramic material is a pre-shaded zirconia ceramic material, the yttrium-containing material is 50% wt to 70% wt, and the application method results in at least 50% or greater transmittance at 700 nm after sintering, when applied to a porous ceramic body comprising the pre-shaded zirconia ceramic material shaped to a target thickness of 1 mm.

Sintered zirconia ceramic bodies treated with a yttrium-containing composition, according to the methods described herein, have biaxial strengths greater than or equal to approximately 500 MPA, greater than or equal to approximately 600 MPA, or greater than or equal to approximately 700 MPA, or greater than or equal to approximately 800 MPA, or greater than or equal to approximately 900 MPa, when measured according to the methods described herein. In one embodiment, a sintered zirconia ceramic body having a biaxial strength greater than 800 MPa has a natural dental restoration shade (Vita Classic Shade for dental restorations) and a percent transmittance (corrected, for sample thickness of 1 mm) that is greater than 45%, or greater than 46% or greater than 47%, or greater than 48%, or greater than 50%, or greater than 52%, or greater than 53%. In one embodiment, the difference in the measured percent transmittance between treated sintered zirconia bodies and untreated sintered zirconia bodies (similarly prepared from equivalent ceramic materials), is greater than 2% transmittance, or greater than 3%, or greater than 4%, or greater than 5% transmittance, or greater than 7%, or greater than 9%, or greater than 10% (corrected; at 700 nm on a 1 mm thick sample). In some embodiments, the L value changes less than 6% or less than 5% or less than 3% in sintered ceramic bodies treated with an yttrium-containing composition compared to similarly prepare, untreated sintered ceramic bodies. In a further embodiment, translucency (percent transmittance at 700 nm) of treated bodies increases while maintaining acceptable L*a*b values in the final sintered body. In one embodiment, the difference in L* values (CIE color space) between an untreated sintered zirconia body and a treated sintered zirconia body is less and or equal to 3%, or less than or equal to 2.5%, or less than or equal to 2%.

Test Methods

Density

The density strongly depends on the composition and structure of the samples of the ceramic materials. Density calculations for ceramic bodies may be determined by liquid displacement method of Archimedes principle. Distilled water was used as the liquid medium. Density of ceramic samples were calculated using the following formula:

$$\rho = \frac{(W^2 - W^1)}{(W^4 - W^1) - (W^3 - W^2)}$$

$\rho$ = Density (gram/cc);

$W1$ = Weight of empty specific gravity bottle (gram);

$W2$ = Weight of specific gravity bottle with sample (gram);

-continued

W3 = Weight of specific gravity bottle with sample and distill water (gram);

W4 = Weight of specific gravity bottle with distill water (gram).

Flexural Strength Test

Flexure tests were performed on sintered test materials using the Instron—Flexural Strength Following ISO 6872 for preparation of strength testing for dental ceramic; flexural strength bar were milled and prepared. Once prepared, the bars were placed centrally on the bearers of the test machine so the load applied to a 4 mm wide face was along a line perpendicular to the long axis of the test piece. Then force is applied and the load needed for breaking the test piece (loading rate was 0.5 mm/min) was recorded. The flexural strength is calculated using sample's dimensional parameter and critical load information.

Flexural strength, σ, in MPa was calculated according to the following formula:

$$\sigma = \frac{3Pl}{2Wb^2}$$

where P is the breaking load, in newton; I is the test span (center-to-center distance between support rollers), in millimeters; w is the width of the specimen, i.e. the dimension of the side at right angles to the direction of the applied load, in millimeters; b is the thickness of the specimen, i.e. the dimension of the side parallel to the direction of the applied load, in millimeters. The mean and standard deviation of the strength was reported. Test bars were prepared by cutting bisque materials taking into consideration the targeted dimensions of the sintered test bars and the enlargement factor (E.F.) of the material, as follows:

starting thickness=3 mm×E.F.;

starting width=4 mm×E.F.;

starting length=35 mm×E.F.

The cut, bisque bars were sintered and flexural strength data was measured and calculated according to the 3 point flexural strength test described in ISO (International Standard) 6872 Dentistry—Ceramic Materials.

Biaxial Strength Test (Piston-On-Three-Ball Test)

Universal mechanical testing machine, capable of a crosshead speed of 1 mm/min (±0.5) and an ability to measure applied loads of between 10 N and 2 500 N (±1%) was used.

The Biaxial flexural strength test fixture had a sample test support of three hardened steel balls with a diameter of (4.5±2) mm positioned 120° apart on a support circle with a diameter of (11±1) mm. The sample was placed concentrically on these supports and the load was applied with a flat punch with a diameter of (1.4±0,2) mm at the center of the sample specimen. The experiment was conducted according to the test method described in ISO (International Standard) 6872 Dentistry—Ceramic Materials.

Translucency

Translucency was measured as percent transmittance. Sample wafers were sectioned from a bisque stage block and machined to a diameter that approximates a final diameter of approximately 30 mm after sintering. Wafers were ground flat until visually free of defects with 1200 and 2000 grit SiC polishing paper. Surface dust was removed and the samples were sintered according to the sintering profile(s) described herein. The final thickness of the bisque body corresponded to a target thickness of approximately 1.0 mm after sintering.

After sintering, sample wafers were briefly washed with isopropanol to remove errant surface material; however, no further surface preparation techniques were applied to the samples prior to testing. Transmission spectra were measured between the wavelengths of 360 nm to 740 nm with a Konica-Minolta CM5 spectrophotometer illuminated by a D65 light source. The spectrophotometer was calibrated to white and black prior to measurement. Translucency samples were placed flush against the (approximately) 24 mm integrating sphere aperture. A minimum of four spectra were collected per sample and averaged to yield a final transmission spectra. Where noted, transmission spectra were corrected for deviations in sample thickness.

Color Space (CIE L*a*b*) Test

Zirconia materials were measured for color space according to CIE L*a*b* (International Commission on Illumination, measuring two polar axes for color, 'a' and 'b', and value (lightness, L)) values using a Konica Minolta Spectrometer with a D65 light source.

27 mm×27 mm sintered test wafers were cut from pre-sintered bisque blocks. The targeted final thickness of the test wafers after sintering was 1.0 mm. Therefore, the starting thickness for each wafer was calculated based on the targeted final thickness taking into consideration the enlargement factor (EF) as follows:

Final thickness×(EF)=bisque wafer thickness.

To measure color, the Konica Minolta Spectrometer was set on reflectance mode, and the L*a*b* values of the sample were measured. These values were referenced to materials made from traditional processes. Color equivalence is indicated if a comparison of ceramic samples made by the methods described herein and traditional methods have a ΔE of less than approximately 3 or less, approximately 2.5 or less, or approximately 2 or less.

Coloring Solutions

Coloring solutions were prepared according to the coloring solutions chart, and mixed in the yttrium-containing compositions, where indicated in the Examples. Coloring solutions (1, 2 and 3) were selected that provided sintered zirconia ceramic bodies having shades that matched commonly requested shades from the Vita Classic shade guide, when applied to an unshaded, bisque body. Approximately 100 grams of a combination of terbium chloride hexahydrate and chromium chloride, and optionally, manganese sulfate were added to form a coloring solution, as described in Table 1.

TABLE 1

Coloring Solutions Chart.

| Solution No. | 100 grams Coloring agent | Propanediol (grams) | Water (grams) | Total salt (wt %) |
|---|---|---|---|---|
| No. 1 | TbCl3, CrCl3 | 429.9 | 20698 | 0.47 |
| No. 2 | TbCl3, CrCl3 | 449.4 | 21637 | 0.45 |
| No. 3 | TbCl3, CrCl3, MnSO4 | 180.1 | 8670 | 1.12 |

Examples 1-6

Unshaded bisque stage zirconia ceramic bodies, treated with yttrium-containing compositions, were sintered and tested for translucency.

Sample wafers were milled from porous, pre-sintered unshaded BruxZir® zirconia milling blanks (unshaded, white 3YSZ) to target a thickness of approximately 1 mm after sintering.

Treatment compositions comprising yttrium chloride hexahydrate were prepared in a range of concentrations from 10 wt. % yttrium chloride (based on the total weight of the treatment composition) to approximately 60 wt % yttrium chloride, as seen in Table 2. No coloring solution was added. Yttrium chloride in water and propanediol were mixed until no more yttrium chloride was visible to the unaided eye, forming the yttrium-containing treatment compositions.

The unshaded bisque zirconia wafers were dipped in the yttrium-containing treatment compositions for approximately 1 to 3 minutes, and then dried, and sintered (substantially according to manufacturer-provided instructions of the zirconia blocks) to approximately full theoretical density.

Figure 3:
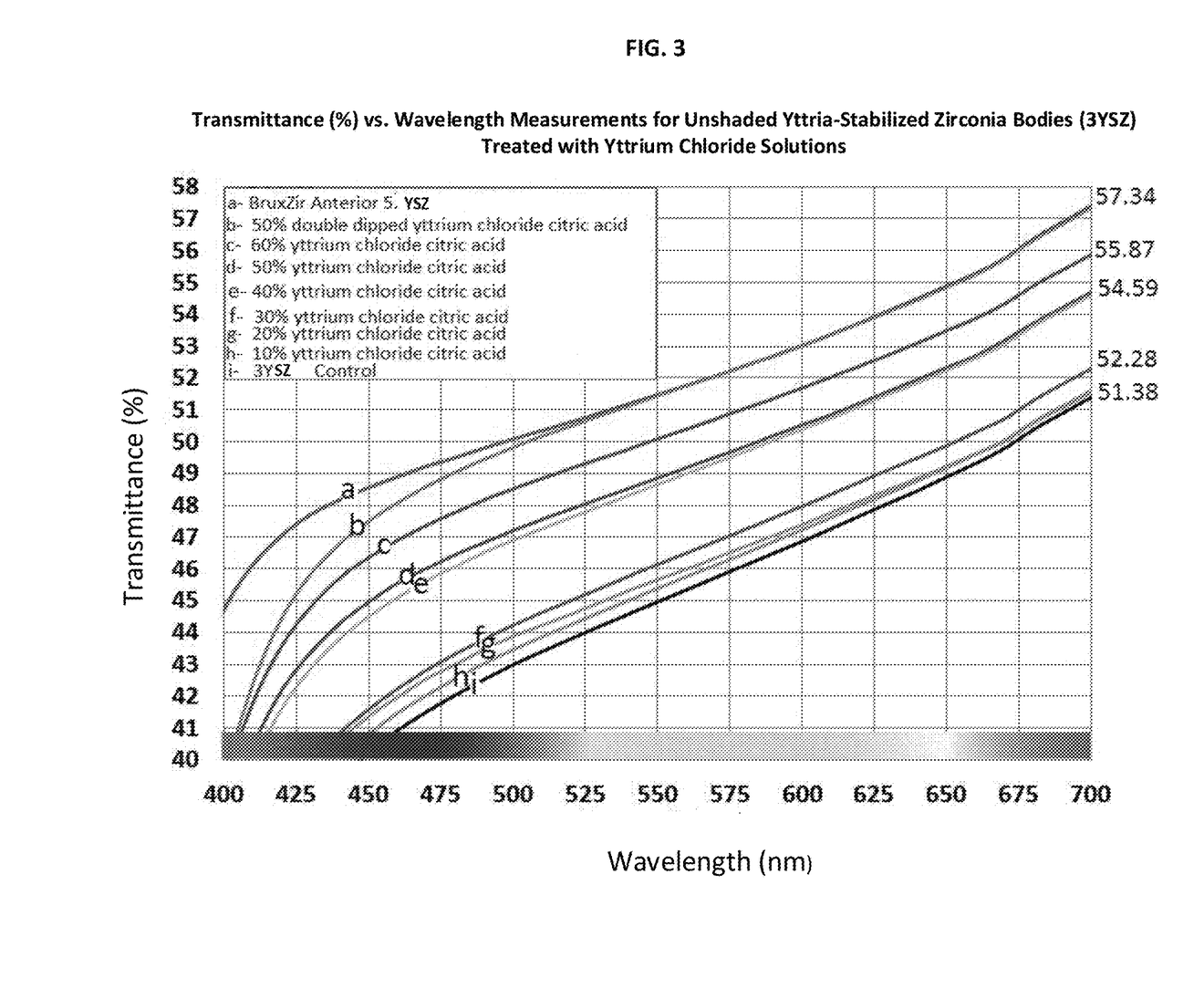
FIG. 3. Graphical representation of transmittance over a wavelength range.

Translucency measurements for treated and untreated unshaded 3 mol % yttria-stabilized zirconia ceramic bodies are shown in FIG. 3 and Table 2, and compared to a control wafers of unshaded zirconia without dipping.

TABLE 2

Translucency (corrected, % Transmittance at 700 nm) of Unshaded Zirconia (3YSZ) Dipped in Yttrium Chloride Compositions.

| Example No. | % Yttrium Chloride (Y)— (no colorant) | % Transmittance at 700 nm |
| --- | --- | --- |
| untreated, unshaded 3YSZ control | — | 51.4 |
| 1 | 10 wt % Y | 51.5 |
| 2 | 20 wt % Y | 52.3 |
| 3 | 30 wt % Y | 51.5 |
| 4 | 40 wt % Y | 54.6 |
| 5 | 50 wt % Y | 54.6; 57.3 ① |
| 6 | 60 wt % Y | 55.9 |

① Zirconia bisque stage sample dipped twice in 50% Yttrium chloride composition.

The difference between percent transmittance of ceramic bodies coated with yttrium-containing compositions comprising greater than or equal to 40 wt. % yttrium compared to untreated sintered ceramic body was greater than 3%, greater than 4%, and greater than 5%.

Examples 7-13

Unshaded zirconia bisque samples, treated with yttrium-containing compositions comprising a colorant, were sintered and tested for translucency.

Sample wafers were prepared from porous, pre-sintered unshaded BruxZir® zirconia milling blanks (unshaded, white YSZ, porous zirconia blanks, 3 mol % yttria stabilized; Glidewell Laboratories, Irvine, CA) by milling to a thickness of approximately 1 mm.

Treatment compositions comprising yttrium-chloride and No. 2 coloring solution were prepared for a range of yttrium chloride concentrations in the manner described above for Examples 1-6. No. 2 coloring solution was provided as described in Table 1, to which an amount of yttrium chloride was added to achieve the approximate weight percent for the solution. Treatment compositions were prepared comprising from approximately 10 wt. % yttrium chloride (based on the total weight of the treatment composition) to approximately 60 wt. % yttrium chloride, as seen in Table 3. No. 2 colorant solution and yttrium chloride were mixed until the yttrium chloride was dissolved, or until no more yttrium chloride was visible to the unaided eye, forming the yttrium-containing treatment compositions.

Unshaded bisque zirconia wafers were dipped in the yttrium-containing treatment compositions for approximately 1 to 3 minutes, and dried. The samples were sintered according to manufacturer-provided instructions to approximately full theoretical density and tested as follows. The samples were compared to a control wafers of unshaded zirconia without the application of the yttrium-containing composition, and dipped in No. 2 coloring solution, only.

Figure 4:
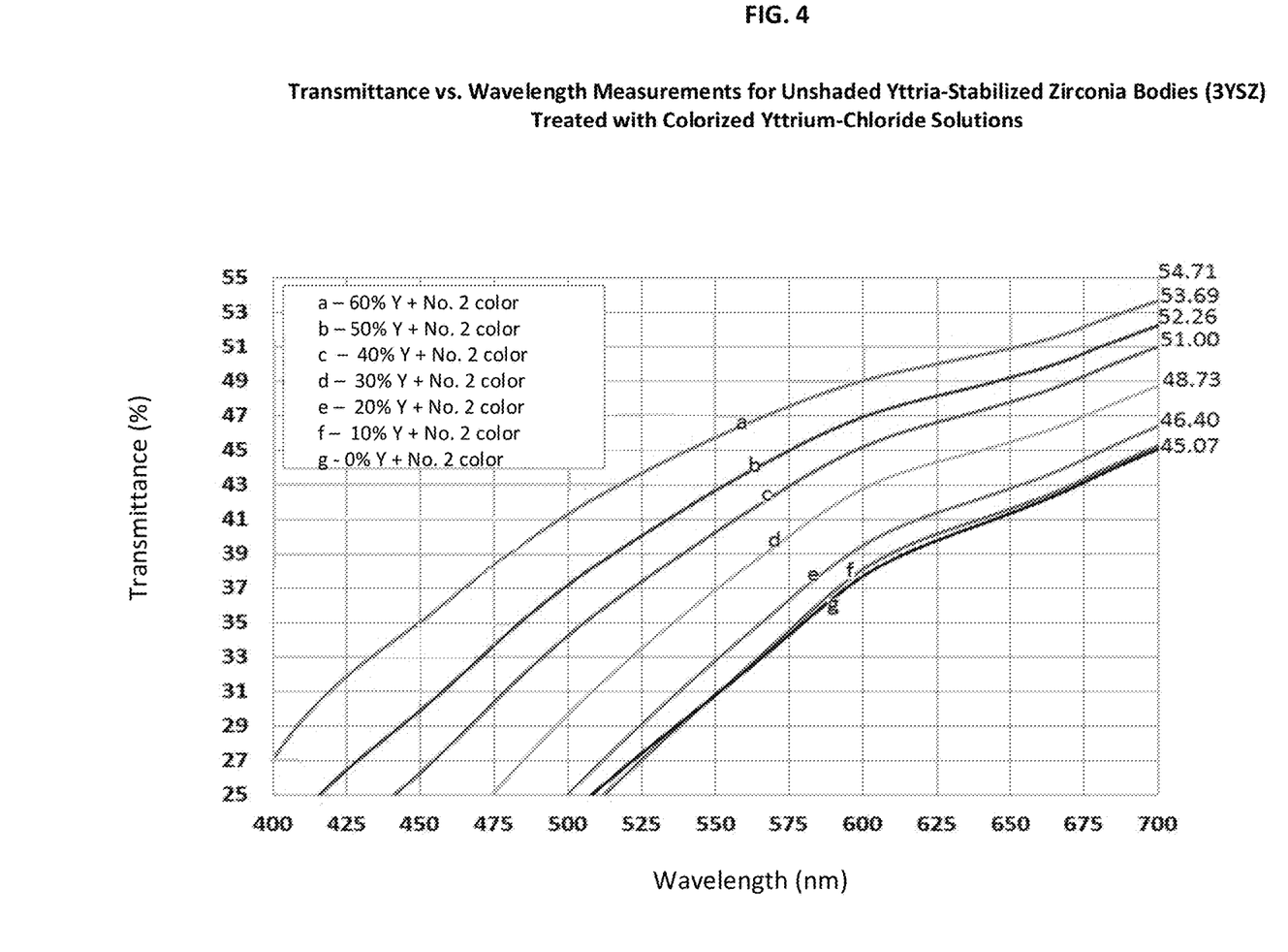
FIG. 4. Graphical representation of transmittance over a wavelength range.

Translucency was measured for treated and untreated unshaded, 3 mol % yttria-stabilized zirconia ceramic bodies, as graphically shown in FIG. 4 and reported in Table 3. Samples were compared to a control wafer that was not dipped in an yttrium-containing composition (3 mol % yttrium-containing composition, 3YSZ), and Ex. 7 which was dipped in the coloring solution, but not the yttrium containing composition.

TABLE 3

Testing of Sintered Zirconia Bodies (white 3YSZ) Treated with Yttrium Chloride Composition with Colorant (No. 2).

| Example No. | Treatment solutions: % yttrium chloride (Y) + color | % Transmittance at 700 nm |
| --- | --- | --- |
| 3YSZ control | — | 52.9 |
| 7 | No. 2 coloring solution only | 45.7 |
| 8 | 10 wt % Y + No. 2 color sol. | 45.3 |
| 9 | 20 wt % Y + No. 2 color sol. | 46.4 |
| 10 | 30 wt % Y + No. 2 color sol. | 48.7 |
| 11 | 40 wt % Y + No. 2 color sol. | 51.0 |
| 12 | 50 wt % Y + No. 2 color sol. | 52.3 |
| 13 | 60 wt % Y + No. 2 color sol. | 53.7 |

Samples dipped in yttrium-containing compositions greater than 10% yttrium formed sintered shaded ceramic bodies having a percent transmittance greater than a sample dipped in coloring solution alone (Example 7). Samples dipped in yttrium-containing compositions comprising coloring solution and yttrium of approximately 50% or greater, upon sintering were shaded and had comparable or better percent transmittance than the unshaded, untreated control (3YSZ control).

Examples 14-18

Porous, unshaded zirconia bisque samples were treated with an yttrium-containing composition comprising a colorant, sintered to full density, and tested for translucency.

Unshaded zirconia ceramic blocks were obtained comprising 3 mol % yttria-stabilized zirconia (Glidewell Laboratories, Irvine, CA). The porous bisque state blocks, and were milled to approximately a 1 mm thick sample size.

Multiple yttrium-containing solutions were prepared as described above for Examples 1-6, comprising from approximately 30 wt. %, approximately 40 wt. %, approximately 50 wt. %, and approximately 60 wt. % yttrium chloride with the addition of an No. 3 coloring solution prepared according to Table 1. The samples were dipped in yttrium-containing solutions for several minutes, and dried. The samples were sintered to approximately full theoretical density according to manufacturer-provided instructions.

Figure 5:
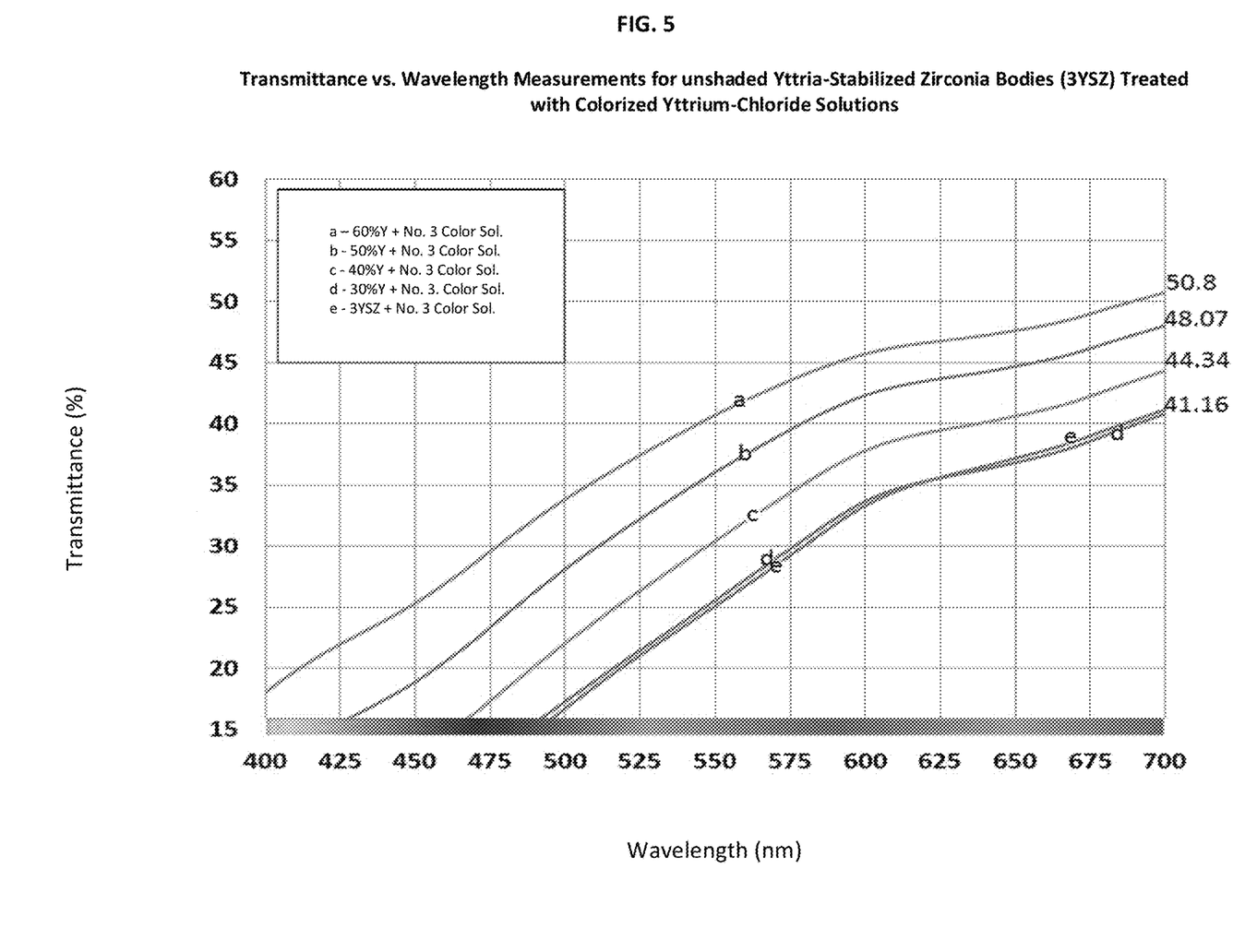
FIG. 5. Graphical representation of transmittance over a wavelength range.

The samples were tested for translucency, measured as percent transmittance according to the methods provided herein, and the results are shown in FIG. 5. The percent transmittance at approximately 700 nm was reported in Table 4.

TABLE 4

Translucency (% Transmittance at 700 nm) of Unshaded Zirconia (3YSZ) Samples Treated with Yttrium Chloride Compositions with Colorant (No. 3).

| Example No. | %Yttrium Chloride (Y) + No. 3 Color Sol. | % Transmittance at 700 nm |
|---|---|---|
| 14 | coloring solution only | 41.2 |
| 15 | 30 wt % Y + No. 3 coloring sol. | 41.2 |
| 16 | 40 wt % Y + No. 3 coloring sol. | 44.3 |
| 17 | 50 wt % Y + No. 3 coloring sol. | 48.1 |
| 18 | 60 wt % Y + No. 3 coloring sol. | 50.1 |

Samples dipped in yttrium-containing compositions greater than or equal to 30% yttrium that comprised coloring solution, were sintered to form shaded ceramic that had greater percent transmittance than Example 14, which was dipped in coloring solution alone.

Examples 19-28

Shaded zirconia bisque samples treated with yttrium-containing compositions comprising a colorant and without a colorant were sintered and tested for translucency and strength.

Sample wafers were milled from porous, pre-sintered shaded BruxZir® milling blanks (Shade 100 zirconia mill blanks, 3YSZ; Glidewell Laboratories, Irvine, CA) to yield a thickness of approximately 1 mm after sintering.

Treatment compositions comprising yttrium-chloride with and without No. 1 coloring solution were prepared comprising a range of yttrium chloride concentrations, as described above for Examples 1-6. No. 1 coloring solution was provided as described in Table 1. Yttrium-containing compositions without coloring solution (Table 5, FIG. 6) and with the addition of coloring solution (Table 6, FIG. 7) were mixed in approximate weight percentages (Tables 5 and 6) until no more yttrium chloride was visible to the unaided eye. Treatment compositions were prepared in a range of concentrations, from approximately 30 wt. % yttrium chloride (based on the total weight of the treatment composition), and approximately 40 wt. %, approximately 50 wt %, approximately 60 wt. %, and approximately 65 wt. % yttrium chloride, as seen in Tables 5 and 6.

Figure 6:
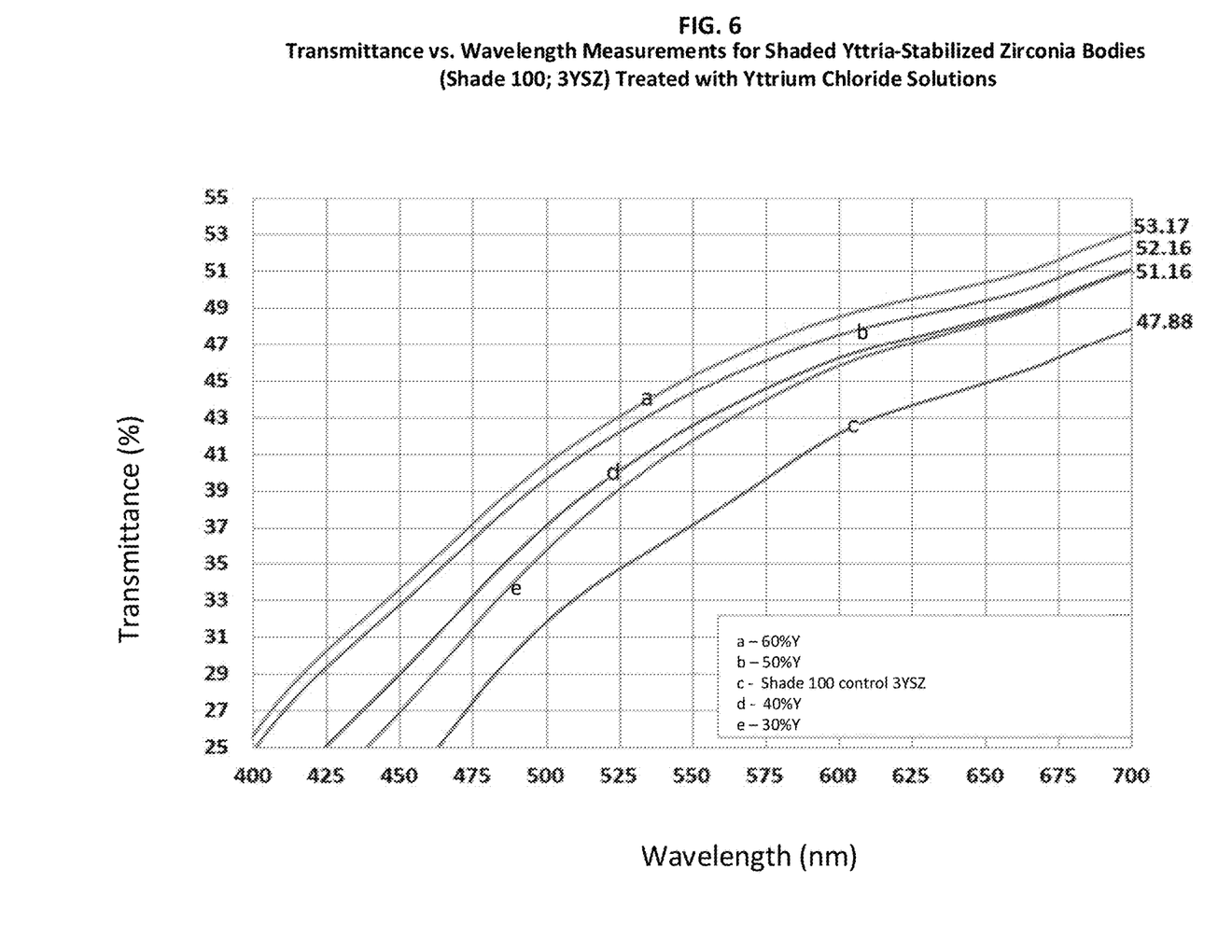
FIG. 6. Graphical representation of transmittance over a wavelength range.
Figure 7:
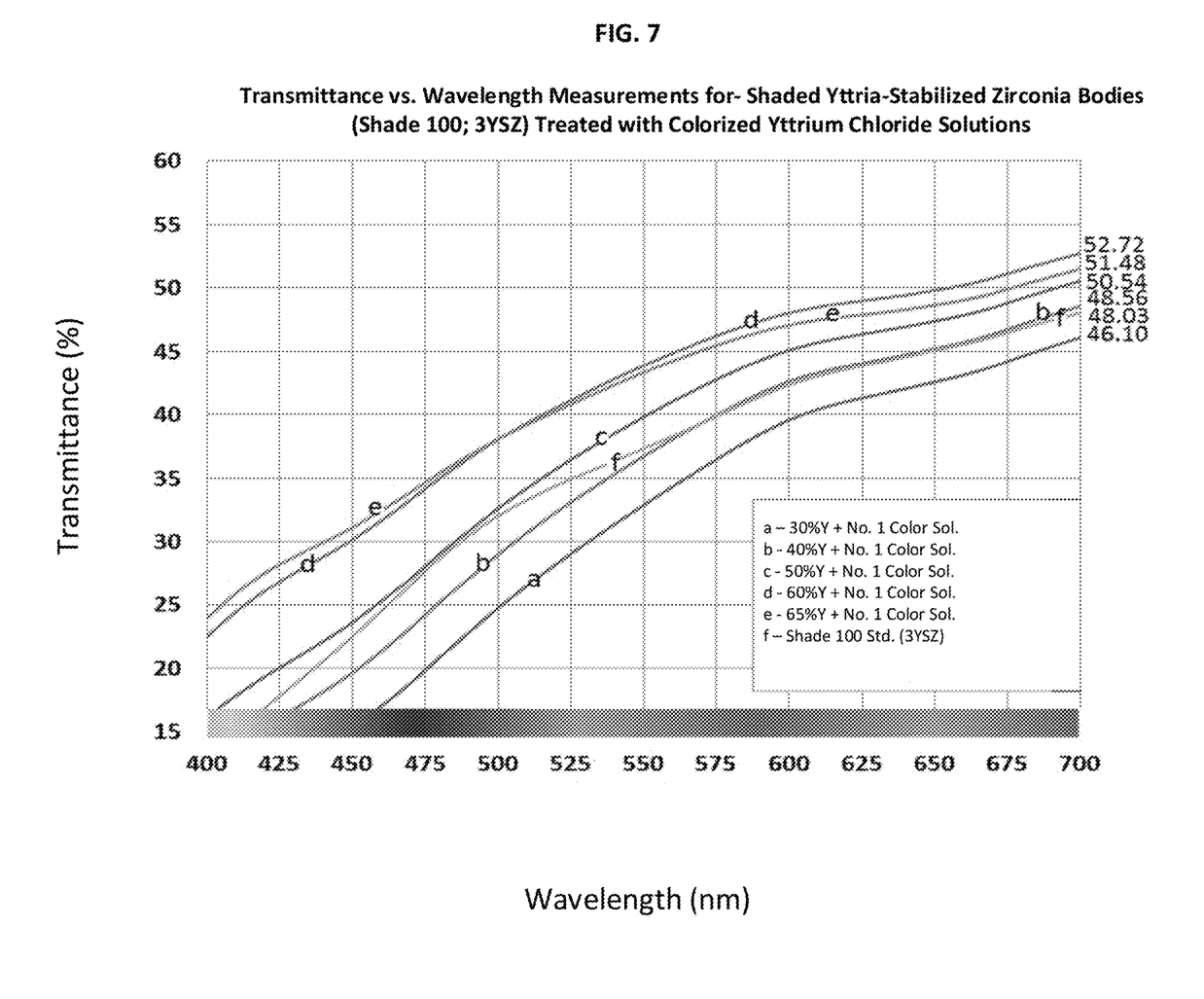
FIG. 7. Graphical representation of transmittance over a wavelength range.

Shaded bisque zirconia wafers were dipped in the yttrium-containing treatment compositions (with and without coloring solution) for approximately 1 to 3 minutes, and then dried. The samples were sintered to full theoretical density. Samples were measured for percent transmittance, as seen in FIG. 6 and FIG. 7, and reported (for 700 nm wavelength) in Table 5 and Table 6. Samples were compared to a control wafers of shaded zirconia not dipped in a treatment composition (47.8% transmittance at 700 nm), and a control wafer (Ex. 23) dipped in No. 1 solution with no yttrium chloride.

TABLE 5

Translucency (% Transmittance at 700 nm) of Shaded Zirconia (Shade 100- 3YSZ) Dipped in Yttrium-Chloride Composition.

| Example No. | % Yttrium Chloride (Y)— No colorant | % Transmittance at 700 nm |
|---|---|---|
| Shade 100 untreated control | — | 47.8 |
| 19 | 30 wt % Y | 51.1 |
| 20 | 40 wt % Y | 51.1 |
| 21 | 50 wt % Y | 52.1 |
| 22 | 60 wt % Y | 53.1 |

Thus, zirconia bisque samples prepared from pre-shaded zirconia powder, that were dipped in yttrium-containing compositions greater than 30% yttrium and that comprised no coloring solution, were sintered to form ceramic bodies having percent transmittance greater than the shaded, untreated zirconia standard (Shade 100 untreated).

TABLE 6

Translucency (% Transmittance at 700 nm) of Shaded Zirconia (Shade 100—3YSZ) Treated with Yttrium-Chloride Composition with Colorant

| Example No. | % Yttrium Chloride + No. 1 Coloring Sol. | % Transmittance at 700 nm |
|---|---|---|
| 23 | coloring sol. only | 48.0 |
| 24 | 30 wt % Y + No. 1 coloring sol. | 46.0 |
| 25 | 40 wt % Y + No. 1 coloring sol. | 48.6 |
| 26 | 50 wt % Y + No. 1 coloring sol. | 50.5 |
| 27 | 60 wt % Y + No. 1 coloring sol. | 52.7 |
| 28 | 65 wt % Y + No. 1 coloring sol. | 51.5 |

Thus, zirconia bisque bodies made from shaded zirconia powder, and then dipped in yttrium-containing compositions (greater than 30% yttrium) that comprised coloring solution, had greater percent transmittance than Example 23, which was a shaded bisque body dipped in coloring solution alone (i.e. without yttrium-chloride).

TABLE 7

Comparison Table of Percent Transmittance of Sintered Zirconia Ceramic Bodies at 700 nm.

| Yttrium-containing Composition % Yttrium Chloride: | Unshaded Zirconia (3YSZ) | | | Shade 100 Zirconia (3YSZ) | |
|---|---|---|---|---|---|
| | Coloring Solution: | | | | |
| | no color | No. 2 col. Sol. | No. 3 col. Sol. | no color | No. 1 col. Sol. |
| 0 wt % YCl3 | 51.4 | 45.1 | 41.2 | 47.8 | — |
| 10 wt % YCl3 | | | — | — | — |
| 20 wt % YCl3 | | | — | — | — |
| 30 wt % YCl3 | | | | | |
| 40 wt % YCl3 | | | | | |
| 50 wt % YCl3 | 54.6 | | | | |
| 60 wt % YCl3 | 55.9 | 53.7 | 50.1 | 53.1 | 52.7 |

Shaded sintered ceramic made from unshaded 3YSZ samples that were treated with yttrium-containing compositions having a colorant had the same or greater translucency than untreated, uncolored white ceramic bodies, when the yttrium-containing composition comprised at least approximately 40 wt. % yttrium chloride or at least approximately 50 wt. % yttrium chloride, and a coloring solution for targeting an No. 2 shade.

Sintered samples made from shaded 3YSZ (Shade 100) and treated with yttrium-containing compositions having at least 30 wt. % yttrium chloride, had approximately the same or greater translucency than untreated, shaded ceramic bodies.

Examples 29-31

Zirconia ceramic bodies prepared with commercially available compositions were compared to both untreated zirconia ceramic bodies and zirconia ceramic bodies using compositions made according to the methods provided herein.

Sample wafers were milled from porous, pre-sintered unshaded BruxZir® milling blanks (unshaded, white porous, 3YSZ bisque blocks, commercially available as BruxZir® 2.0 blanks; Glidewell Laboratories, Irvine, CA) to a thickness of approximately 1 mm.

An yttrium-containing composition comprising 60 wt. %. yttrium chloride in a 1M citric acid solution was prepared, as described above for Examples 1-6. No colorant was added. Commercially available liquid compositions were obtained (Chang's Liquid—Old Translucency and Young Translucency; IDS CAD, Luray, VA).

Figure 8:
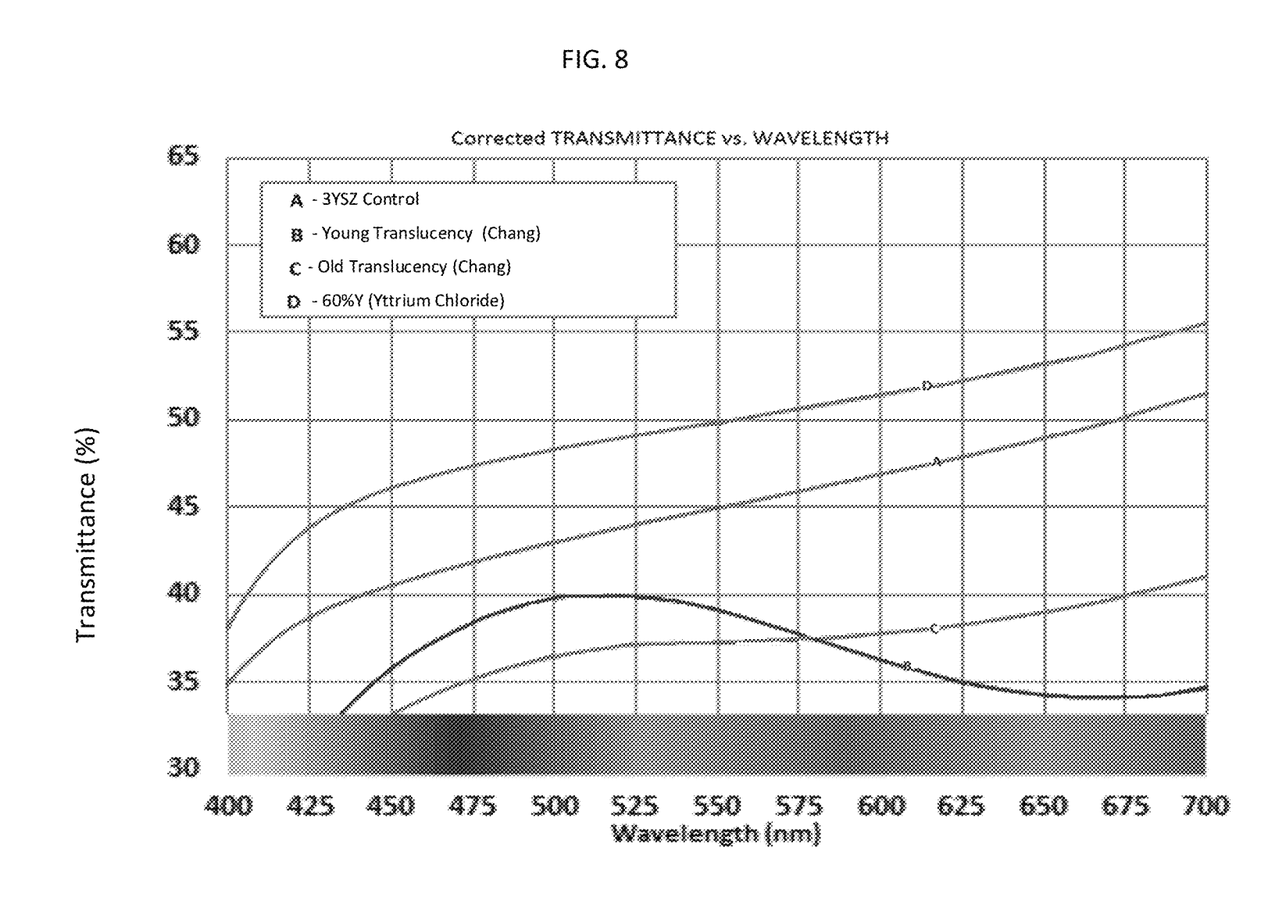
FIG. 8. Graphical representation of transmittance over a wavelength range.

Sample wafers were coated by brushing with each composition in a similar manner, and then dried. After sintering to approximately full theoretical density according to manufacturer-provided instructions, samples were tested for translucency. Transmittance was corrected for sample thickness, and may be seen in FIG. 8. At 700 nm, Example 29, zirconia ceramic body treated with 60 wt. % yttrium chloride in 1M citric acid had a corrected transmittance of approximately 56%, and the untreated zirconia ceramic body had a corrected transmittance of approximately 52%. Example 30 and 31, zirconia ceramic body treated with the commercially available translucency enhancing liquids (Old Translucency Effect and Young Translucency effect, respectively) had a corrected transmittance of approximately 42% and 34% transmittance at 700 nm.

Examples 32-37

Shaded zirconia bisque samples treated with yttrium-containing compositions comprising a colorant were sintered and tested for translucency (as percent transmittance).

Porous, pre-sintered 4 mol % yttria-stabilized zirconia blocks were made from powder (Tosoh USA) shaded to approximate the appearance of Vita Classical A2 in a sintered restoration. The blocks were pre-sintered to a bisque stage, and then, accommodating for shrinkage during sintering, bisque blocks were milled into the shape of wafers having a thickness that yields about a 1 mm thick wafer after sintering.

Treatment compositions comprising yttrium-chloride with No. 1 coloring solution were prepared comprising a range of yttrium chloride concentrations. No. 1 coloring solution was provided as described in Table 1, and diluted to a concentration of approximately 33.3% wt. coloring solution. Yttrium-containing compositions were added to the 33.3% No. 1 coloring solution in amounts to achieve between 10 wt. % and 50 wt. % (Table 8), based on the total weight of the yttrium-containing compositions and mixed until no more yttrium chloride was visible to the unaided eye. Bisque zirconia wafers were dipped in the yttrium-containing treatment compositions for approximately 1 to 3 minutes, and then dried.

The samples of Examples 32-35 and Example 37 were sintered to full theoretical, according to the sintering profile, as follows: heating the sintering oven in which treated samples are placed from about 25° C. to about 1200° C. in about 78 minutes, and having a dwell time of about 60 minutes at 1200° C.; heating from about 1200° C. to about 1300° C. in about 50 minutes; heating from about 1300° to about 1530° C. in about 28 minutes, and having a dwell time of about 150 minutes at 1530° C.; and cooling the oven from about 1530° C. to about 155° C. in about 90 minutes. Example 36 was sintered substantially similarly, except that the oven was heated from about 1300° C. to about 1500° C. in about 28 minutes.

Figure 9:
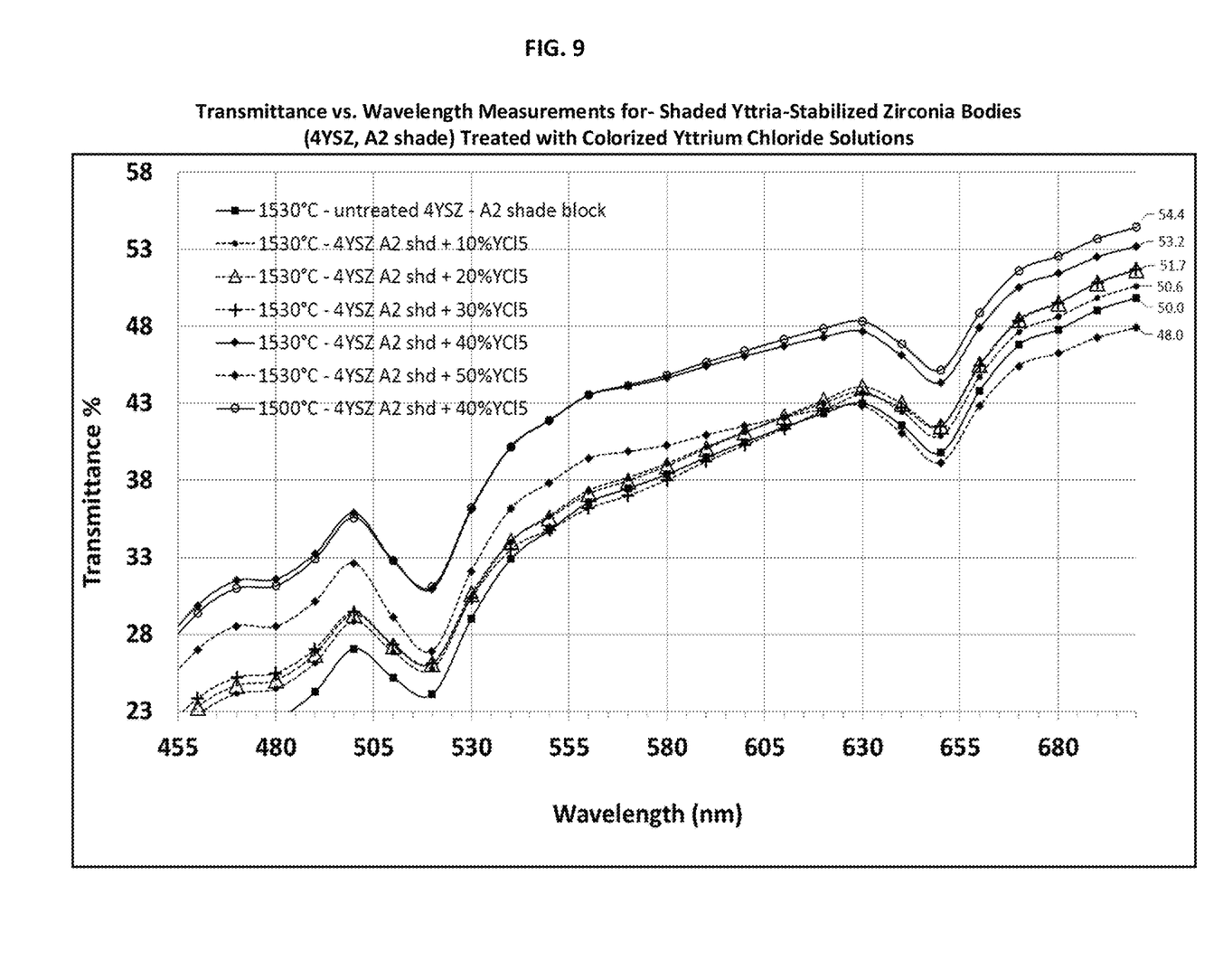
FIG. 9. Graphical representation of transmittance over a wavelength range.

Samples were measured for percent transmittance, as seen in FIG. 9, and reported (for 700 nm wavelength, corrected for thickness) in Table 8. Samples were compared to a control wafers of shaded zirconia (4YSZ, in A2 target shade) that was not dipped in a treatment composition (approximately 50.0% transmittance at 700 nm).

TABLE 8

Translucency (% Transmittance at 700 nm) of Shaded Zirconia (4YSZ in A2-equivalent Shade) Dipped in Yttrium-Chloride Composition.

| Example No. | % Yttrium Chloride (Y) + No. 1 Colorant | % Transmittance at 700 nm |
| --- | --- | --- |
| 4YS—A2-Shade ceramic; untreated | — | 50 |
| 32 | 10 wt % Y | 50.6 |
| 33 | 20 wt % Y | 51.7 |
| 34 | 30 wt % Y | 51.7 |
| 35 | 40 wt % Y (1530° C.) | 53.2 |
| 36 | 40 wt % Y (1500° C.) | 54.4 |
| 37 | 50 wt % Y | 48.0 |

Zirconia bisque samples prepared from pre-shaded zirconia powder that were dipped in compositions containing between 10 wt. % yttrium and 40 wt. % yttrium-containing composition comprising a coloring solution, were sintered to form ceramic bodies having percent transmittance greater than the shaded, untreated zirconia control (4YSZ, A2 target shade).

We claim:

1. A method for enhancing the translucency of a sintered zirconia dental restoration comprising
    obtaining a porous zirconia ceramic body that comprises an yttria-stabilized zirconia material comprising 2 mol % yttria to 7 mol % yttria;
    obtaining an aqueous yttrium-containing composition comprising
        between 20% wt and 70% wt yttrium-containing material and
        a colorant comprising at least one metal-containing component as a coloring agent; and
    providing a first application of the yttrium-containing composition to penetrate a portion of the porous zirconia ceramic body;
    providing a second application of the yttrium-containing composition to penetrate the portion of the porous zirconia ceramic body that comprises the aqueous yttrium-containing composition of the first application; and
    sintering the porous zirconia ceramic body after the first and second application to form a sintered zirconia dental restoration;
    wherein a difference in L* values (CIE color space) between (i) the sintered zirconia dental restoration having the first and second applications of the yttrium-containing composition and (ii) an untreated sintered zirconia dental restoration is less than or equal to 6%.

2. The method of claim 1 wherein the yttria-stabilized zirconia material is a pre-shaded zirconia ceramic material.

3. The method of claim 1, wherein the yttria-stabilized zirconia material is a pre-shaded zirconia ceramic material and the yttrium-containing composition comprises between 40 wt. % and 70 wt. % of the yttrium-containing material.

4. The method of claim 1, wherein the yttria-stabilized zirconia material is a pre-shaded zirconia ceramic material comprising from 3 mol % yttria to 5 mol % yttria, and the yttrium-containing composition comprises between 20 wt. % and 40 wt. % of an yttrium-chloride.

5. The method of claim 1, wherein the yttria-stabilized zirconia material is an unshaded, white zirconia ceramic material and the yttrium-containing composition comprises from 20 wt. % to 65 wt. % of the yttrium-containing material based on the total weight of yttrium-containing composition.

6. The method of claim 1, wherein the at least one metal-containing component of the colorant comprises one or more metals selected from terbium, erbium, chromium, cobalt and manganese.

7. The method of claim 6, wherein the colorant comprises one or more coloring agents selected from terbium chloride, chromium chloride, and manganese sulfate.

8. The method of claim 1, wherein the colorant comprises 0.05 wt. % to 2 wt. % of a metallic salt as a coloring agent, based on the total weight of the yttrium-containing composition.

9. The method of claim 1, wherein the porous zirconia ceramic body has a density of 50% to 90% of full theoretical density.

10. The method of claim 1, wherein the yttria-stabilized zirconia ceramic material comprises 85 wt. % to 100 wt. % of a zirconia ceramic material.

11. The method of claim 1, wherein the porous zirconia ceramic body is in the shape of a dental restoration having an incisal edge and a facial surface.

12. The method of claim 11, comprising applying the yttrium-containing composition to the facial surface of the dental restoration from an incisal edge to a distance of one-third to one-half the length of the facial surface proximate the incisal edge, and the applying the second application to penetrate a portion of the porous ceramic body that comprises the aqueous yttrium-containing composition from the first application.

13. The method of claim 11, wherein the first application is applied to the facial surface from the incisal edge for a first distance of 1 mm to 5 mm from the incisal edge, and the second application is applied to the facial surface from the incisal edge for a second distance of 0.5 mm to 3 mm and is less than the first distance.

14. The method of claim 1, further comprising the step of penetrating through the thickness of the ceramic body with the yttrium-containing composition.

15. The method of claim 1, wherein the sintered body has an yttria concentration gradient wherein the yttria concentration is increasingly lower as the distance from the incisal edge increases.

16. A method for applying an yttria-containing composition to enhance optical properties of a sintered zirconia ceramic body, comprising an application method comprising
applying a first application of an aqueous yttria-containing composition to an edge of a porous ceramic dental restoration form comprising an yttria-stabilized zirconia ceramic material for a first application distance of 1 mm to 5 mm from the edge, and penetrating a portion of the porous ceramic dental form;
applying a second application of the yttria-containing composition to the edge for a second application distance of 0.5 mm to 3 mm from the edge, penetrating the portion of the porous ceramic dental restoration form containing the aqueous yttria-containing composition from the first application, wherein the second application distance is less than the first application distance; and
sintering the porous ceramic dental restoration form after the first and second application to form a dental restoration;
wherein the yttrium-containing composition comprises between 30% wt and 70% wt yttrium-containing material and a colorant comprising at least one metal-containing component as a coloring agent; and
wherein the application method provides at least 46% or greater transmittance at 700 nm when applied to a porous zirconia ceramic body made from the yttria-stabilized zirconia ceramic material having a 1 mm target thickness when sintered to at least 98% theoretical density; and
wherein a difference in L* values (CIE color space) between (i) a sintered zirconia ceramic body having the first and second applications of the yttrium-containing composition and (ii) an untreated zirconia ceramic body is less than or equal to 6%.

17. The method of claim 16, wherein the porous, yttria-stabilized zirconia ceramic material is a pre-shaded zirconia ceramic material, the yttrium-containing material is between 40% wt and 70% wt, and the application method provides at least 50% or greater transmittance at 700 nm after sintering, when applied to the porous zirconia ceramic body made from the yttria-stabilized zirconia ceramic material shaped to a target thickness of 1 mm when sintered.

18. The method of claim 16, wherein the porous, yttria-stabilized zirconia ceramic material is a pre-shaded zirconia ceramic material, the yttrium-containing material is between 50% wt and 70% wt, and the application method results in at least 50% or greater transmittance at 700 nm after sintering, when applied to the porous zirconia ceramic body made from the yttria-stabilized zirconia ceramic material shaped to a target thickness of 1 mm when sintered.

* * * * *